(12) United States Patent
Nakayama et al.

(10) Patent No.: US 10,271,801 B2
(45) Date of Patent: Apr. 30, 2019

(54) RADIATION IMAGING SYSTEM, IMAGE PROCESSING DEVICE, AND IMAGE PROCESSING PROGRAM

(71) Applicant: FUJIFILM Corporation, Tokyo (JP)

(72) Inventors: Hiroki Nakayama, Ashigarakami-gun (JP); Tomoki Inoue, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 727 days.

(21) Appl. No.: 14/865,836

(22) Filed: Sep. 25, 2015

(65) Prior Publication Data

US 2016/0089098 A1 Mar. 31, 2016

(30) Foreign Application Priority Data

Sep. 26, 2014 (JP) ................................ 2014-197318

(51) Int. Cl.
| | | |
|---|---|---|
| *A61B 5/00* | (2006.01) | |
| *A61B 6/02* | (2006.01) | |
| *A61B 6/00* | (2006.01) | |
| *A61B 6/04* | (2006.01) | |
| *A61B 6/12* | (2006.01) | |
| *A61B 10/04* | (2006.01) | |

(52) U.S. Cl.
CPC ............ *A61B 6/025* (2013.01); *A61B 6/0414* (2013.01); *A61B 6/12* (2013.01); *A61B 6/467* (2013.01); *A61B 6/488* (2013.01); *A61B 6/502* (2013.01); *A61B 6/461* (2013.01); *A61B 6/5205* (2013.01); *A61B 2010/045* (2013.01)

(58) Field of Classification Search
CPC ......... A61B 6/025; A61B 6/488; A61B 6/467; A61B 6/12; A61B 6/0414; A61B 6/502; A61B 2010/045; A61B 6/461; A61B 6/5205
See application file for complete search history.

(56) References Cited

U.S. PATENT DOCUMENTS

2006/0120505 A1* 6/2006 Seto ...................... A61B 6/12
378/4

FOREIGN PATENT DOCUMENTS

| JP | 2006-158634 A | 6/2006 |
|---|---|---|
| JP | 2013-169360 A | 9/2013 |

* cited by examiner

*Primary Examiner* — Joel Lamprecht
(74) *Attorney, Agent, or Firm* — Birch, Stewart, Kolasch & Birch, LLP

(57) ABSTRACT

Disclosed are a radiation imaging system, an image processing device, and a non-transitory computer-readable recording medium having an image processing program recorded thereon which facilitate the confirmation of a positional relationship between an object of interest and a biopsy needle. A control unit of a console reconstructs a projection image obtained by tomosynthesis imaging to generate a tomographic image parallel (an x-y-axis direction) to an imaging surface in a state where a needle is inserted into a breast, and specifies an image of an object of interest from the tomographic image. The control unit generates a sectional image which includes the specified image of the object of interest and an image of the needle and intersects the imaging surface. The control unit generates an image of the needle from the projection image, synthesizes the generated image of the needle into the sectional image while aligning, and displays the sectional image.

20 Claims, 9 Drawing Sheets

RADIATION IMAGING SYSTEM 10

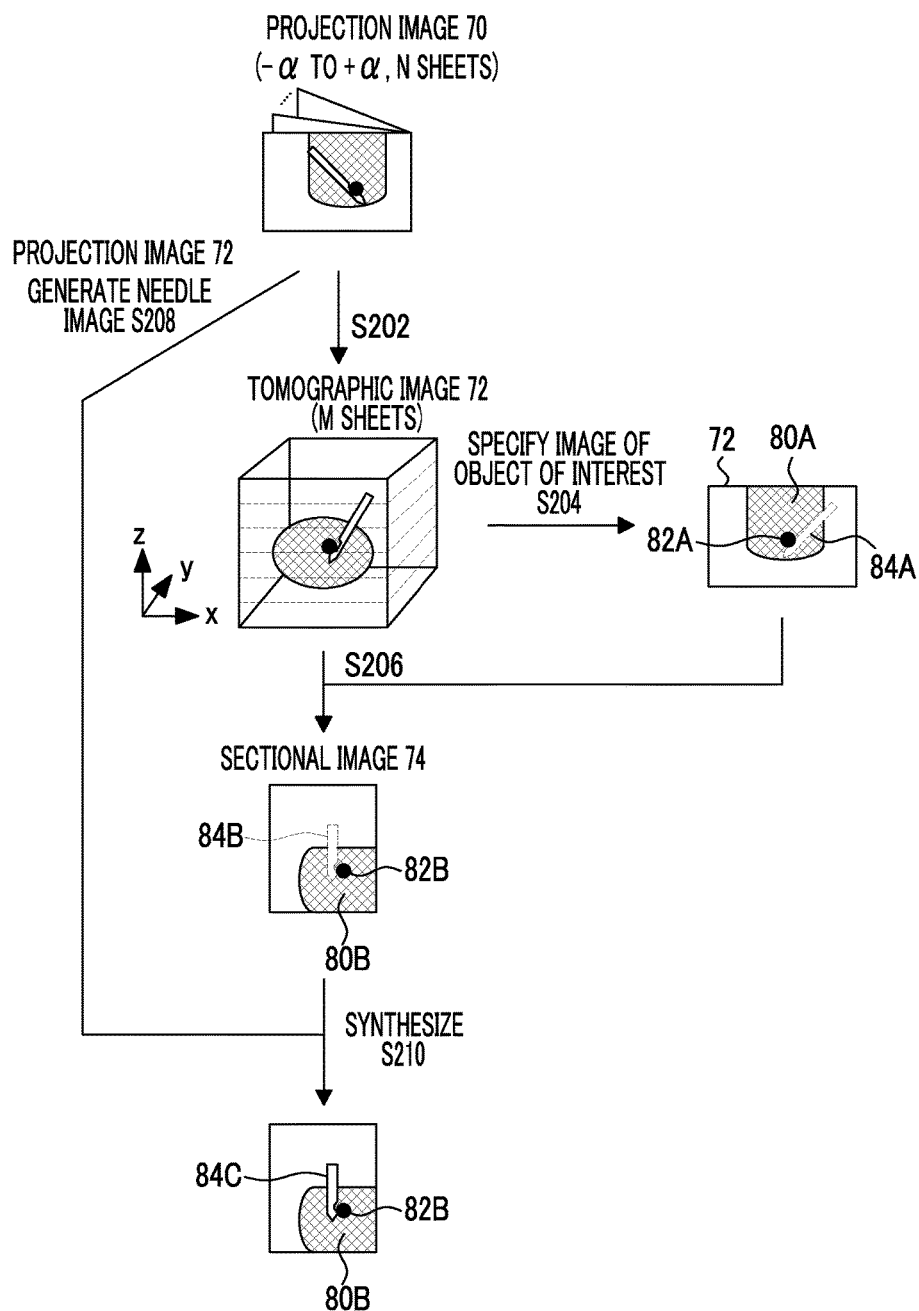

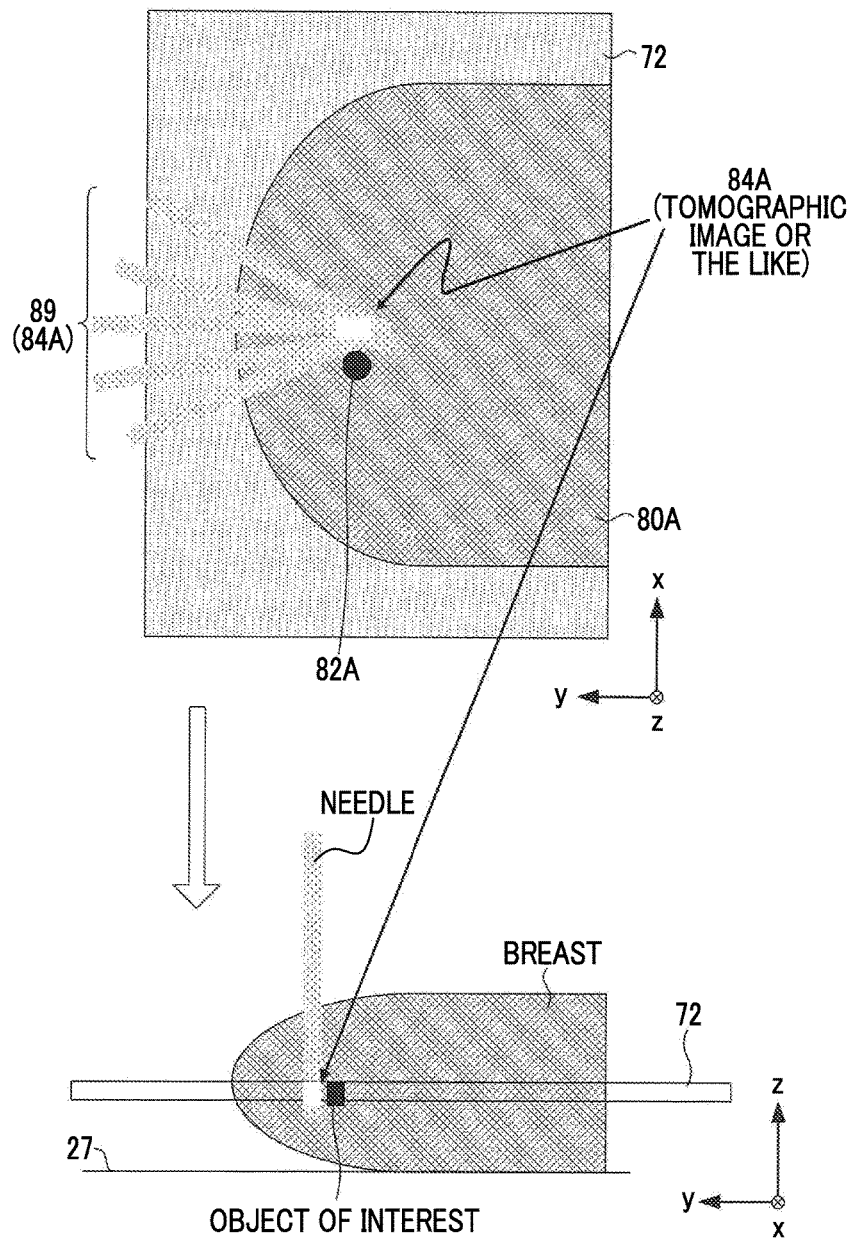

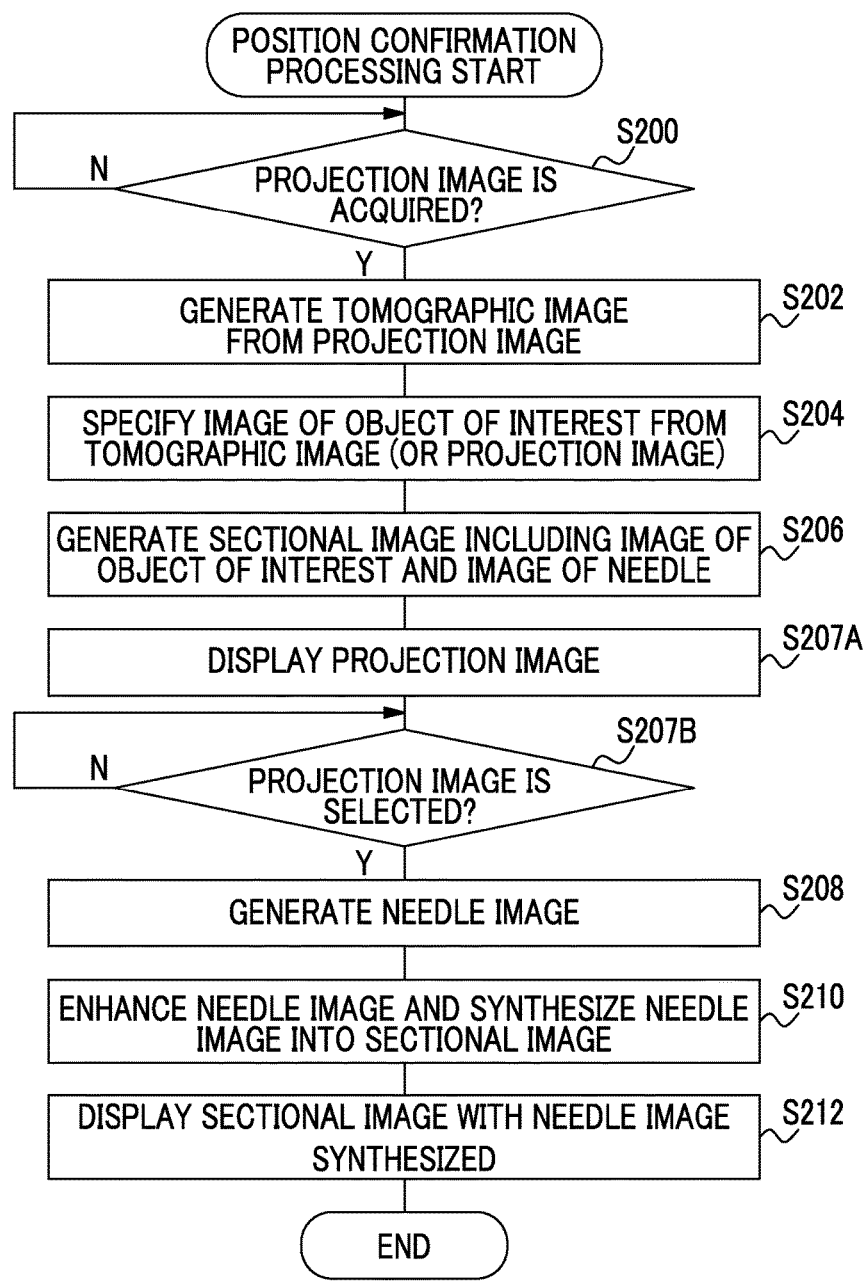

RADIATION IMAGING SYSTEM, IMAGE PROCESSING DEVICE, AND IMAGE PROCESSING PROGRAM

CROSS-REFERENCE TO RELATED APPLICATIONS

The present application claims priority under 35 U.S.C. § 119 to Japanese Patent Application No. 2014-197318, filed on Sep. 26, 2014. Each of the above application(s) is hereby expressly incorporated by reference, in its entirety, into the present application.

BACKGROUND OF THE INVENTION

1. Field of the Invention

The present invention relates to a radiation imaging system, an image processing device, and a non-transitory computer-readable recording medium having an image processing program recorded thereon.

2. Description of the Related Art

As a radiation imaging device which captures a radiation image, so-called mammography which captures a radiation image of a breast of a patient to be a subject is known. Furthermore, as an imaging method, tomosynthesis imaging in which radiation is exposed to a breast from a plurality of directions to capture a radiation image, and a tomographic image is generated based on the captured radiation image is known.

For the purpose of medical diagnosis, a biological examination (biopsy) in which a part of an object of interest of a patient is collected by a biopsy needle is generally performed. When performing a biopsy, in order to appropriately collect an object of interest, a radiation image is captured in a state where the biopsy needle is inserted into the patient, and the positional relationship between the object of interest and the biopsy needle is confirmed by the captured radiation image.

When performing a biopsy, as a technique for confirming the positional relationship between the object of interest and the biopsy needle by a computed tomography (CT) image or a radiation image, for example, the techniques described in JP2006-158634A and JP2013-169360A are known.

SUMMARY OF THE INVENTION

However, in the related art, it may be difficult to obtain an image in which both the biopsy needle and the object of interest have high visibility, and it may be difficult to confirm the positional relationship between the object of interest and the biopsy needle.

An object of the invention is to provide a radiation imaging system, an image processing device, and a non-transitory computer-readable recording medium having an image processing program recorded thereon which facilitate the confirmation of the positional relationship between an object of interest and a biopsy needle.

In order to attain the above-described object, a radiation imaging system of the invention includes a radiation imaging device which includes a radiation detector configured to detect radiation and an imaging stand configured to include the radiation detector, and exposes a breast in a state where the breast placed on an imaging surface of the imaging stand and a biopsy needle inserted into the breast to radiation at each of different projection angles to capture a plurality of projection images by the radiation detector, a tomographic image generation unit which generates a plurality of tomographic images based on the plurality of captured projection images, a specification unit which specifies an image of an object of interest from one of the projection image captured from a direction normal to the imaging surface, the tomographic image generated by the tomographic image generation unit, and a pseudo two-dimensional image reconstructed based on the tomographic image, a sectional image generation unit which generates a sectional image of a section intersecting the imaging surface and including an image according to the object of interest specified by the specification unit, and a synthesis unit which generates an image of the biopsy needle and synthesizes the generated image of the biopsy needle on the sectional image generated by the sectional image generation unit.

In the radiation imaging system of the invention, the sectional image generation unit may generate a sectional image including an image according to the object of interest specified by the specification unit and an image according to the inserted biopsy needle, and the synthesis unit may further generate an image of the biopsy needle and synthesizes the image of the biopsy needle on the image of the biopsy needle in the sectional image.

In the radiation imaging system of the invention, the sectional image generation unit may reproject the plurality of tomographic images generated by the tomographic image generation unit onto a section in a direction intersecting the imaging surface to generate the sectional image.

In the radiation imaging system of the invention, the synthesis unit may extract and generate the image of the biopsy needle from one of the plurality of projection images and synthesizes the image of the biopsy needle into the sectional image.

In the radiation imaging system of the invention, the synthesis unit may extract the image of the biopsy needle from a projection image corresponding to a projection angle which is the greatest projection angle among the different projection angles and corresponds to a side separated from the biopsy needle.

In the radiation imaging system of the invention, the section may be a surface in a direction perpendicular to the imaging surface.

The radiation imaging system of the invention may further include a reception unit which receives the designation of an image of an object of interest from one of the projection image, the tomographic image, and the pseudo two-dimensional image, and the specification unit may specify the image of the object of interest based on the designation of the image of the object of interest received by the reception unit.

In the radiation imaging system of the invention, the synthesis unit may perform enhancement processing for enhancing the image of the biopsy needle to be synthesized.

The radiation imaging system of the invention may include a display unit which displays the sectional image with the image of the biopsy needle synthesized by the synthesis unit.

In the radiation imaging system of the invention, the synthesis unit may display the plurality of projection images on the display unit, the radiation imaging system may further include a designation unit which receives the designation of a projection image used to generate the image of the biopsy needle from the plurality of displayed projection images, and the synthesis unit may generate the image of the biopsy needle from the projection image received by the designation unit.

A radiation imaging system of the invention includes a radiation imaging device which includes a radiation detector configured to detect radiation and an imaging stand configured to include the radiation detector, and exposes a breast in a state where the breast placed on an imaging surface of the imaging stand and a biopsy needle inserted into the breast to radiation at respective different projection angles to capture a plurality of projection images at the respective projection angles by the radiation detector, a specification unit which specifies an image of an object of interest from the projection image captured in a direction normal to the imaging surface, a sectional image generation unit which generates a sectional image of a section intersecting the imaging surface and including an image according to the object of interest specified by the specification unit, and a synthesis unit which generates an image of the biopsy needle, synthesizes the generated image of the biopsy needle on the sectional image generated by the sectional image generation unit, and displays the synthesized sectional image on a display unit.

An image processing device of the invention which is used in the above-described radiation imaging system includes the tomographic image generation unit which generates the plurality of tomographic images reconstructed based on projection images obtained by imaging the breast at different projection angles in a state where the biopsy needle collecting the object of interest is inserted into the breast, the specification unit which specifies the image of the object of interest from one of the projection image, the tomographic image, and the pseudo two-dimensional image reconstructed based on the tomographic image, the sectional image generation unit which generates the sectional image of the section intersecting the tomographic image and including the image according to the object of interest specified by the specification unit, and the synthesis unit which generates the image of the biopsy needle, synthesizes the generated image of the biopsy needle on the sectional image generated by the sectional image generation unit, and displays the synthesized sectional image on a display unit.

There is provided a non-transitory computer-readable recording medium having an image processing program of the invention recorded thereon, the image processing program causing a computer to execute processing for acquiring the plurality of projection images from the radiation imaging device which includes the radiation detector configured to detect radiation and the imaging stand configured to include the radiation detector, and exposes the breast in a state where the breast placed on an imaging surface of the imaging stand and the biopsy needle inserted into the breast to radiation at each of different projection angles to capture the plurality of projection images by the radiation detector, generating the plurality of tomographic images based on the plurality of captured projection images, specifying the image of the object of interest from one of the projection image captured in the direction normal to the imaging surface, the tomographic image, and the pseudo two-dimensional image reconstructed based on the tomographic image, generating the sectional image of the section intersecting the imaging surface and including the specified image according to the object of interest, and generating the image of the biopsy needle and synthesizing the generated image of the biopsy needle on the sectional image.

According to the invention, the effect of facilitating the confirmation of the positional relationship between the object of interest and the biopsy needle is obtained.

BRIEF DESCRIPTION OF THE DRAWINGS

FIG. 7 is an explanatory view illustrating an example of position confirmation processing of the first embodiment.

FIG. 8 is a schematic view of an example of a tomographic image having an image of a breast, an image of an object of interest, and an image of a needle.

FIG. 9 is a flowchart showing an example of position confirmation processing which is executed by a control unit of a console of a second embodiment.

DESCRIPTION OF THE PREFERRED EMBODIMENTS

Figure 1:
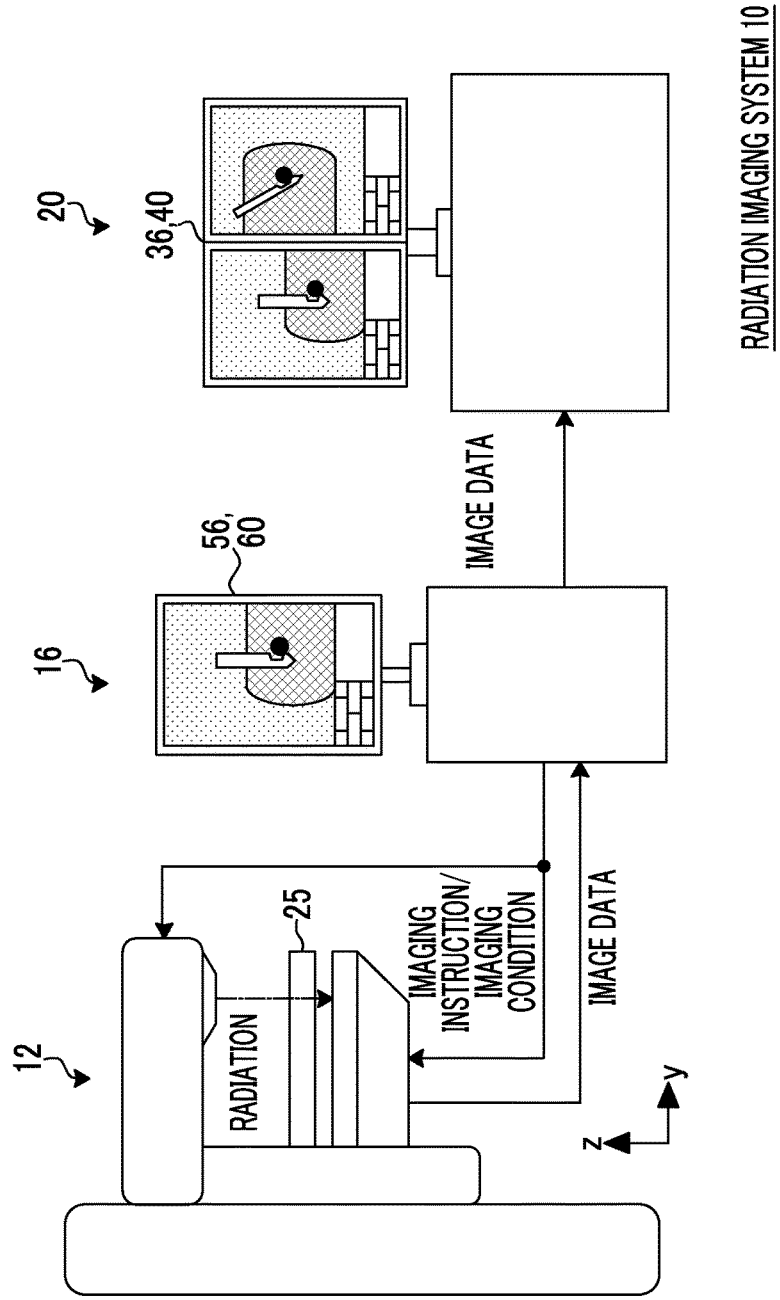
FIG. 1 is a schematic configuration diagram showing the outline of the overall configuration of an example of a radiation imaging system of a first embodiment.

Hereinafter, an embodiment of the invention will be described in detail referring to the drawings. This embodiment is not intended to limit the invention.

Figure 2:
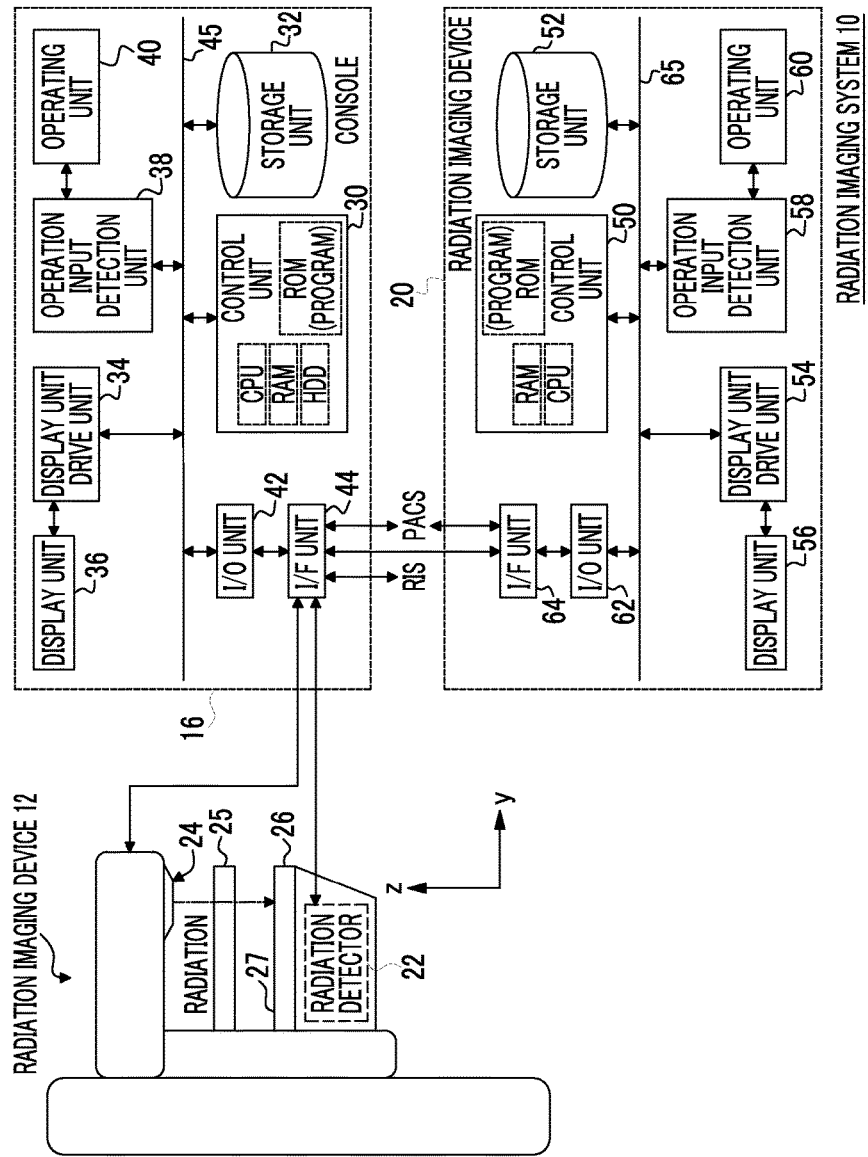
FIG. 2 is a schematic configuration diagram illustrating functions of an example of a console and a radiation imaging device in the radiation imaging system of the first embodiment.

First, the schematic configuration of the entire radiation imaging system of this embodiment will be described. FIG. 1 is a schematic configuration diagram of an example of the overall configuration of the radiation imaging system of this embodiment. FIG. 2 is a schematic configuration diagram illustrating functions of an example of a console 16 and a radiation image reading device 20 in the radiation imaging system of this embodiment.

The radiation imaging system 10 of this embodiment has a function of capturing a radiation image by an operation from a user, such as a physician or a radiology technician, based on an instruction (imaging menu) input from an external system (for example, a radiology information system (RIS)) through the console 16.

The radiation imaging system 10 of this embodiment includes a radiation imaging device 12, the console 16, and the radiation image reading device 20.

In the radiation imaging system 10 of this embodiment, a case where the console 16 generates and displays a tomographic image based on a radiation image captured through tomosynthesis imaging by the radiation imaging device 12 will be described. In this embodiment, a radiation image obtained through tomosynthesis imaging by a radiation detector 22 of the radiation imaging device 12 is referred to as a "projection image". A radiation image reconstructed based on the "projection image" is referred to as a "tomographic image". Furthermore, an image which includes the "projection image", the "tomographic image", and a "sectional image" described below, and is obtained by subjecting image processing to an image captured using radiation is collectively referred to as a "radiation image".

The radiation imaging device 12 of the embodiment is a device which captures a radiation image of a breast of a subject, and is, for example, mammography. The radiation imaging device 12 may be a device which images the breast of the subject in a sitting state where the subject sits on a chair (including a wheelchair) or the like. The radiation imaging device 12 may be a device which is capable of individually imaging the right and left breasts of the subject in a state where at least the upper body of the subject is upright.

The radiation imaging device 12 has a radiation source 24, such as a tube lamp, which is provided to face an imaging surface 27 of an imaging stand 26, and exposes radiation from the radiation source 24 toward the imaging surface 27.

When capturing the radiation image of the breast of the subject, one breast as an object is compressed with a compression plate 25 with respect to the imaging surface 27 of the imaging stand 26 and fixed, and radiation is exposed from the radiation source 24 to the fixed breast. The compression plate 25 compresses the breast with respect to the imaging surface 27, and a member which transmits radiation is used as the compression plate.

Figure 3:
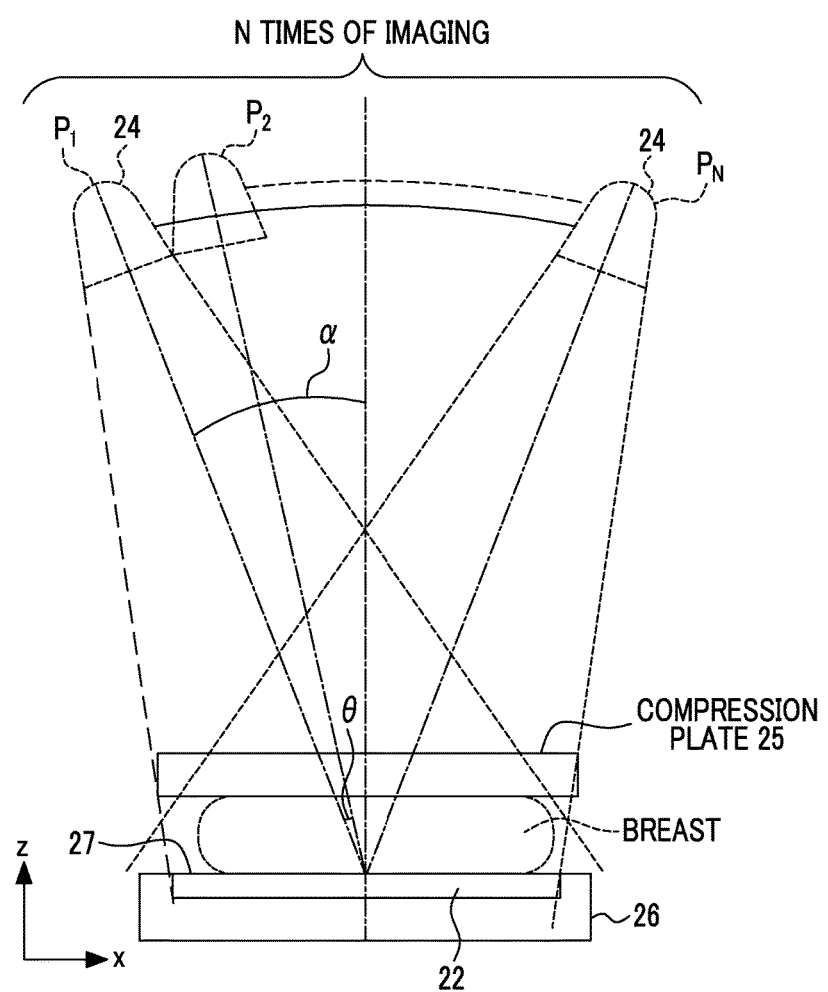
FIG. 3 is an explanatory view illustrating tomosynthesis imaging in the radiation imaging device of the first embodiment.

The radiation imaging device 12 of this embodiment is a device which is capable of performing imaging of at least a breast as an object at a plurality of projection angles (directions) by moving the radiation source 24, so-called tomosynthesis imaging. FIG. 3 is an explanatory view illustrating tomosynthesis imaging in the radiation imaging device 12 of this embodiment. In the radiation imaging device 12, as shown in FIG. 3, when performing imaging (tomosynthesis imaging) of a breast at a plurality of projection angles, the radiation source 24 moves in an arc shape along an X-axis direction. In this embodiment, as shown in FIG. 3, imaging is performed at N places P1 to PN as the position of the radiation source 24 while moving an imaging position by a predetermined angle θ from an angle α. Furthermore, in the radiation imaging device 12 of this embodiment, the direction from the imaging stand 26 side on which the object is brought into contact with the breast to back side of the device is referred to as the "y-axis direction", the direction parallel to the imaging surface 27 and intersecting the y-axis direction is referred to as the "x-axis direction", and the direction normal to the imaging surface 27 is referred to as the "z-axis direction".

Inside the imaging stand 26, the radiation detector 22 to which radiation transmitted through the breast as the object and the imaging surface 27 is exposed and which detects radiation is arranged. Radiation detected by the radiation detector 22 is visualized and a radiation image is generated. The radiation detector 22 receives exposure of radiation with image data carried thereon, records image data representing a radiation image, outputs recorded image data, and detects an electric charge of each pixel generated according to the dose of exposed radiation as image data. The radiation detector 22 of this embodiment is a flat panel detector (FPD), and is, for example, a direct conversion type panel using a Se layer where an electron is directly generated by exposed radiation. The radiation detector 22 is not limited to the direct conversion type panel, and an indirect conversion type panel or an electronic cassette may be used.

The radiation imaging device 12 of this embodiment is a device which is capable of collecting an object of interest, such as a tumor or calcification in the subject (breast), by a biopsy needle. Hereinafter, a case where an object of interest is collected using a needle as an example of a biopsy needle will be described. In this embodiment, a person, such as a physician, who performs observation, diagnosis, and the like of an object of interest, such as a tumor, by a captured radiation image is referred to as a "user", and a target to be observed, such as a tumor or calcification, of the user is referred to as an "object of interest". The collection of the object of interest is referred to as a "biopsy". In this embodiment, when performing a biopsy, tomosynthesis imaging is performed in a state where the needle is inserted into the object, and the user confirms the positional relationship between the object of interest and the needle (whether or not the needle is at an appropriate position for collecting the object of interest) from the obtained radiation image.

In this embodiment, image data representing a radiation image output from the radiation detector 22 of the radiation imaging device 12 is transmitted to the console 16. The console 16 of this embodiment has a function of controlling the radiation imaging device 12 using an imaging menu, various kinds of information, and the like acquired from an external system or the like through a wireless communication local area network (LAN) or the like. Furthermore, the console 16 of this embodiment has a function of transmitting and receiving various kinds of information to and from the radiation detector 22 of the radiation imaging device 12. Furthermore, the console 16 of this embodiment has a function of generating and displaying a tomographic image based on the radiation image acquired from the radiation detector 22. In addition, the console 16 of this embodiment has a function of transmitting the radiation image acquired from the radiation detector 22 or the generated tomographic image to the radiation image reading device 20.

The console 16 of this embodiment is an example of an image processing device, and is a server computer. As shown in FIG. 2, the console 16 includes a control unit 30, a storage unit 32, a display unit drive unit 34, a display unit 36, an operation input detection unit 38, an operating unit 40, an input/output (I/O) unit 42, and an interface (I/F) unit 44. The control unit 30, the storage unit 32, the display unit drive unit 34, the operation input detection unit 38, and the I/O unit 42 are connected so as to transmit and receive information and the like to and from one another through a bus 45, such as a system bus or a control bus.

The control unit 30 of this embodiment is an example of a tomographic image generation unit, a specification unit, a sectional image generation unit, and a synthesis unit. The control unit 30 has a function of controlling the operation of the entire console 16. Furthermore, the control unit 30 has a function of performing the generation of a tomographic image, the generation of a sectional image, and the like based on a projection image obtained through tomosynthesis imaging. The control unit 30 of this embodiment includes a central processing unit (CPU), a read only memory (ROM), a random access memory (RAM), and a hard disk drive (HDD). The CPU has a function of controlling the entire operation of the console 16. The ROM stores various programs and the like used in the CPU in advance. The RAM has a function of temporarily storing various kinds of data. The HDD has a function of storing and saving various kinds of data. The HDD may be a solid state drive (SDD) or may be used as the storage unit 32.

The display unit drive unit 34 has a function of controlling display of various kinds of information on the display unit 36. The display unit 36 of this embodiment has a function of displaying the imaging menu, image data, the radiation image, and the like. The operation input detection unit 38 has a function of detecting an operation state of the operating unit 40 or a processing operation on the operating unit 40. The operating unit 40 is used when the user issues an instruction relating to imaging of the radiation image, the generation of the tomographic image, and the like. The operating unit 40 may have a keyboard or a mouse as an example, or may be have a touch panel integrated with the display unit 36. Furthermore, the operating unit 40 may include a camera, and may have a function of inputting various instructions by making the camera recognize the gestures of the user.

The I/O unit 42 and the I/F unit 44 have a function of transmitting and receiving various kinds of information to and from an external system, such as the radiation imaging device 12 (the radiation source 24, the radiation detector 22, and the like), the radiation image reading device 20, or an RIS, and an external system, such as a picture archiving and communication system (PACS), by wireless communication or wired communication.

The storage unit 32 has a function of storing various kinds of data including image data, the radiation image, and the like received from the radiation detector 22.

The radiation image reading device 20 has a function of receiving image data, the radiation image, and the like from the console 16 and displaying the received image data, the radiation image, and the like. As a specific example of the radiation image reading device 20, a viewer or the like is given; however, the radiation image reading device 20 is not particularly limited, and a portable information terminal device which is a so-called personal digital assistance (PDA) represented by a tablet terminal, a smartphone, or the like may be used.

As shown in FIG. 2, the radiation image reading device 20 of this embodiment includes a control unit 50, a storage unit 52, a display unit drive unit 54, a display unit 56, an operation input detection unit 58, an operating unit 60, an I/O unit 62, and an I/F unit 64. The control unit 50, the storage unit 52, the display unit drive unit 54, the operation input detection unit 58, and the I/O unit 62 are connected so as to transmit and receive information and the like to and from one another through a bus 65, such as a system bus or a control bus.

The control unit 50 has a function of controlling the operation of the entire radiation image reading device 20. The control unit 50 includes a CPU, a ROM, and a RAM. The CPU has a function of controlling the operation of the entire radiation image reading device 20. The ROM stores various processing programs and the like used in the CPU in advance. The RAM has a function of temporarily storing various kinds of data.

The display unit drive unit 54 has a function of controlling display of various kinds of information including image data, the radiation image, and the like on the display unit 56. The operation input detection unit 58 has a function of detecting an operation state of the operating unit 60 or a processing operation on the operating unit 60. In this embodiment, the operating unit 60 is used when the user issues an instruction to the radiation image displayed on the display unit 56. In this embodiment, the operating unit 60 includes, for example, a touch panel, a touch pen, a plurality of keys, a mouse, and the like. When the operating unit 60 is constituted of a touch panel, the display unit 56 may have a touch panel and may include the function of the operating unit 60.

The I/O unit 62 and the I/F unit 64 have a function of performing communication of various kinds of communication with the console 16 or the PACS through wireless communication by electric waves, optical communication by light, or the like.

The storage unit 52 has a function of storing the radiation image received from the console 16. As a specific example of the storage unit 52, a nonvolatile memory or the like is given.

In this embodiment, various programs stored in the control unit 30 of the console 16 and the control unit 50 of the radiation image reading device 20 are stored in the ROMs of the control unit 30 and the control unit 50 in advance. However, the storage locations of various programs are not limited thereto, and various programs may be stored in a recording medium, such as a compact disk read only memory (CD-ROM) or a removable disk and may be installed from the recording medium on the ROM or the like. Furthermore, various programs may be installed from an external device on the ROM or the like through a communication line, such as the Internet.

Next, the action of the radiation imaging system 10 of this embodiment will be described referring to the drawings.

Figure 4:
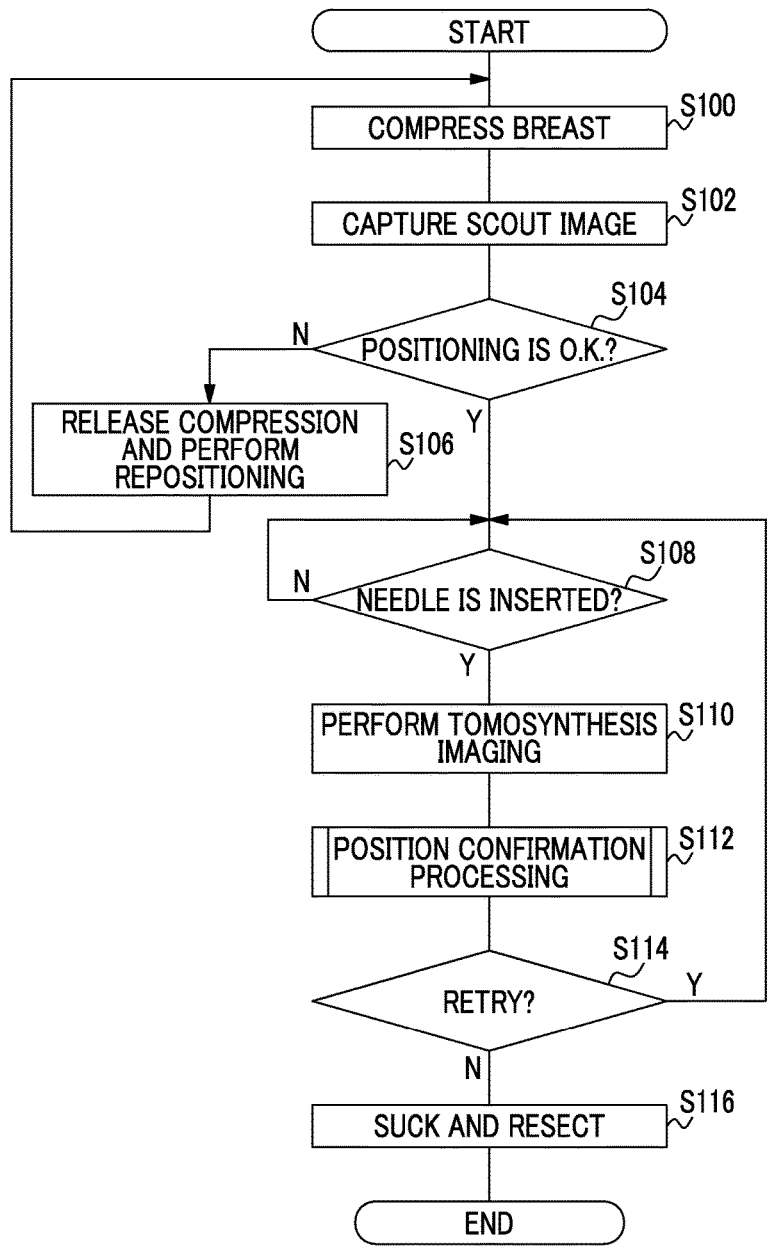
FIG. 4 is a flowchart showing an example of a biopsy in the radiation imaging system of the first embodiment.

FIG. 4 is a flowchart showing an example of the flow of a biopsy in the radiation imaging system 10 of this embodiment.

In the radiation imaging system 10, when capturing the radiation image, imaging is executed according to the imaging menu. When information for instructing a "biopsy" is included in the imaging menu, the control unit 30 of the console 16 determines to perform a biopsy and executes the biopsy according to the flowchart shown in FIG. 4.

In Step S100, the control unit 30 of the console 16 instructs the radiation imaging device 12 to compress the breast of the subject with the compression plate 25. The subject brings one breast to be an object into contact with the imaging surface 27 of the radiation imaging device 12. The control unit 30 of the console 16 instructs the radiation imaging device 12 to move the compression plate 25 toward the imaging surface 27. In the radiation imaging device 12, the breast is fixed by the compression plate 25.

Next, in Step S102, in order to confirm positioning, capturing a scout image where radiation is exposed such that the optical axis of radiation is normal to the imaging surface 27, that is, at an angle of 0°, without rotating (moving) the radiation source 24 is performed. The control unit 30 of the console 16 instructs the radiation imaging device 12 to capture the scout image. The user confirms whether or not positioning is appropriate by the scout image captured by the radiation imaging device 12.

Next, in Step S104, the control unit 30 of the console 16 determines whether or not positioning is appropriate (O.K.). When it is determined from the scout image that positioning is inappropriate, the user instructs the effect with the operating unit 40. When it is instructed that positioning is inappropriate, the process progresses to Step S106. In Step S106, after the compression of the breast with the compression plate 25 is released, the control unit 30 of the console 16 returns to Step S100. If the compression is released, the user repositions the breast. With the release of the compression of the breast, processing for prompting repositioning (for example, displaying a message for prompting repositioning on the display unit 36) or the like may be performed.

When the confirmation of positioning is not performed, the processing of Step S102 to Step S106 may be omitted.

When positioning is appropriate, the process progresses from Step S104 to Step S108. In Step S108, it is determined whether or not the needle is inserted. The insertion of the needle for collecting an object of interest in the breast is performed by the physician as the user. The needle is normally inserted at an angle and a direction intersecting a plurality of tomographic images obliquely with respect to the imaging surface 27.

When a biopsy unit (not shown) is provided in the radiation imaging device 12, the user may use the biopsy unit upon inserting the needle. If the needle is inserted to a collection position (specifically, a planned collection position) of the object of interest, a completion instruction to the effect of the completion of the insertion is performed by, for example, the operating unit 40. The control unit 30 of the console 16 is in a standby state that the completion instruction is issued, and if the completion instruction is issued, progresses to Step S110.

Figure 5:
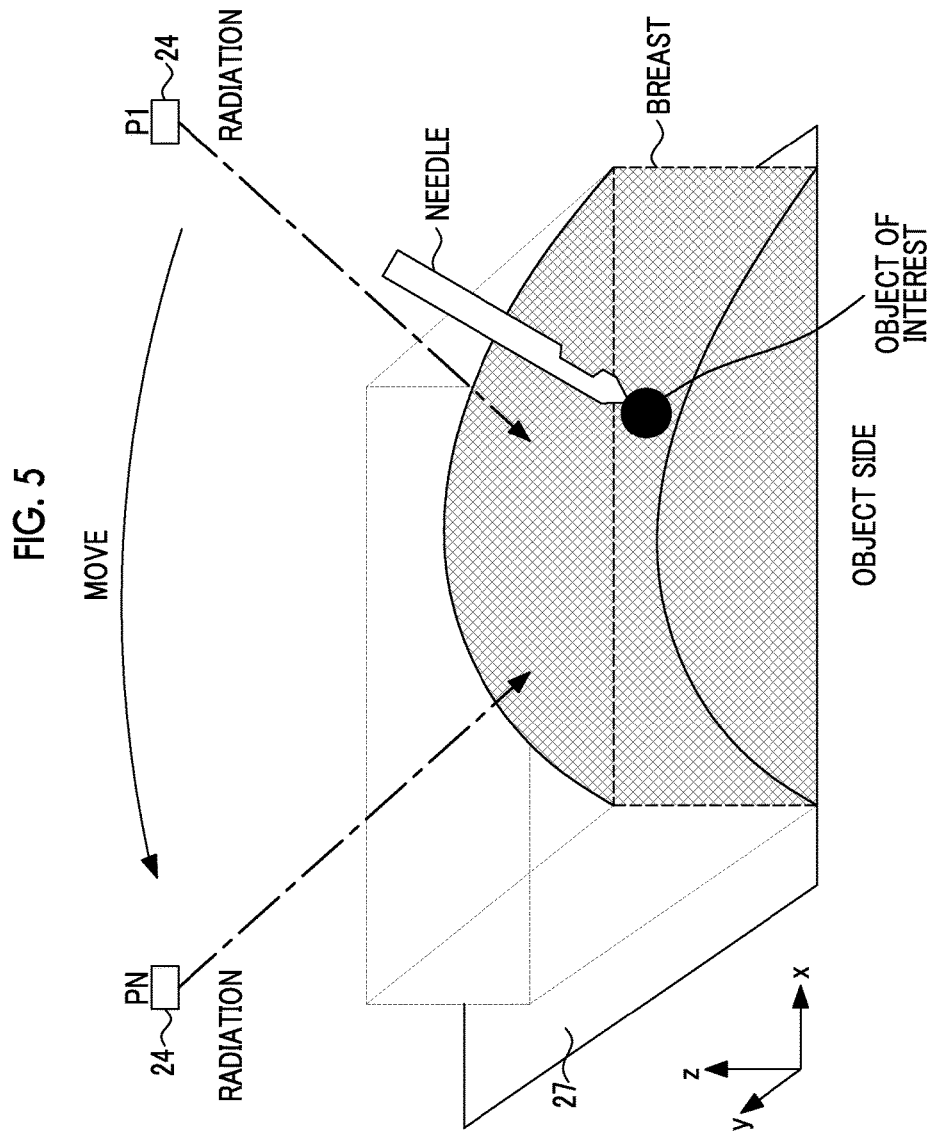
FIG. 5 is a schematic view of tomosynthesis imaging in a state where a needle is inserted into a breast.

If the insertion of the needle is completed, in Step S110, the control unit 30 of the console 16 instructs the radiation imaging device 12 to perform tomosynthesis imaging. When an imaging instruction to perform tomosynthesis imaging where imaging is performed on the breast from a plurality of directions is input, the radiation imaging device 12 of this embodiment performs imaging while moving the radiation source 24 in an arc shape along the x-axis direction without moving the imaging stand 26. Specifically, as shown in FIG. 3, exposure of radiation based on respective imaging conditions is performed at N places of P1 to PN as the position of the radiation source 24 while moving the imaging position by the predetermined angle θ from the angle α. Radiation individually exposed from the radiation source 24 is transmitted through the breast and then reaches the radiation detector 22. FIG. 5 is a schematic view of tomosynthesis imaging in a state where the needle is inserted into the breast. As shown in FIG. 5, the needle is generally inserted in a direction intersecting a plurality of tomographic images described below in detail obliquely with respect to the imaging surface 27.

If radiation is exposed, the radiation detector 22 outputs image data representing the exposed radiation image (projection image) to the console 16. As described above, when exposure of radiation is performed at N places of P1 to PN as the position of the radiation source 24, image data of N sheets of projection images is output to the console 16.

Figure 6:
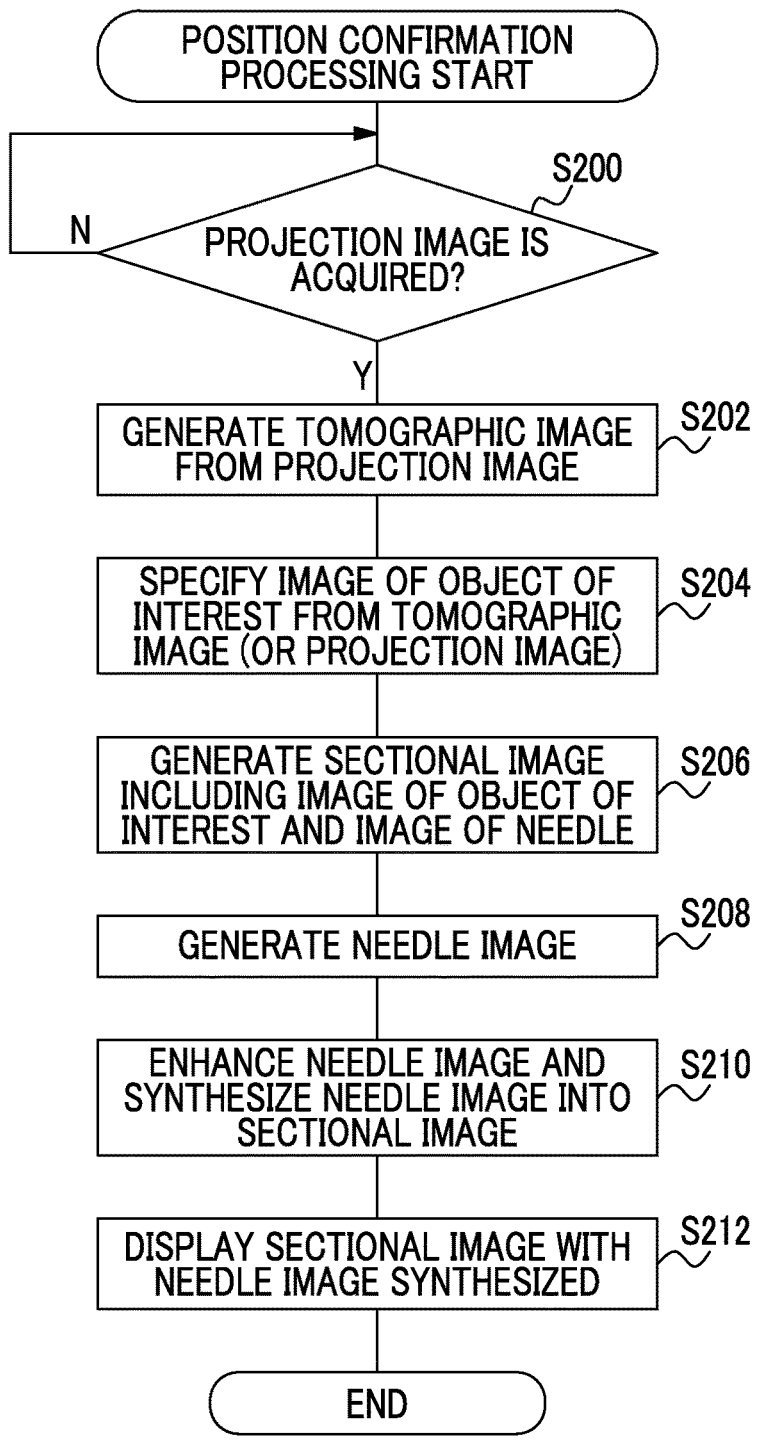
FIG. 6 is a flowchart showing an example of position confirmation processing which is executed by a control unit of the console of the first embodiment.

Next, in Step S112, the control unit 30 of the console 16 performs position confirmation processing for the positional relationship between the object of interest and the needle. FIG. 6 is a flowchart showing an example of position confirmation processing which is executed by the control unit 30 of the console 16 of this embodiment. FIG. 7 is an explanatory view illustrating an example of position confirmation processing.

In Step S200, the control unit 30 of the console 16 determines whether or not N sheets of projection images (FIG. 7, projection images 70) are acquired. The control unit 30 of the console 16 can recognize the number of projection images 70 captured through tomosynthesis imaging from the imaging menu and the like. In this step, the control unit 30 determines whether or not all projection images 70 captured through tomosynthesis imaging are acquired from the radiation detector 22. When the projection images are not acquired, the standby state is placed, and when the projection images are acquired, the process progresses to Step S202.

In Step S202, the control unit 30 of the console 16 reconstructs a tomographic image (FIG. 7, a tomographic image 72) based on a plurality of acquired projection images 70 to generate a tomographic image 72 parallel to the imaging surface 27 at a predetermined slice thickness. In this embodiment, the term "parallel" includes "substantially parallel". FIG. 7 shows, as a specific example, a case where the control unit 30 generates M sheets of tomographic images 72.

The position where the object of interest is projected on the projection image 70 differs depending on the projection angle at which the radiation source 24 exposes radiation from each position. Accordingly, in the control unit 30, the amount of movement of the object of interest among a plurality of projection images 70 is calculated based on the projection angle at which the projection image 70 is captured, and the reconstruction of the tomographic image 72 is performed based on a known reconstruction method. The projection angle may be acquired from the imaging menu, or may be acquired from the radiation imaging device 12 (radiation detector 22) in association with each projection image 70.

The control unit 30 displays the generated tomographic images 72 on the display unit 36. A way of displaying is not particularly limited, and the tomographic images 72 may be sequentially displayed according to a slice position, or a plurality of tomographic images 72 may be simultaneously displayed on the display unit 36. At least a part of the M sheets of tomographic images 72 has an image 80A of the breast, an image 82A of the object of interest, and an image 84A of the needle like the tomographic image 72 shown in FIG. 7.

In this embodiment, the image 84A of the needle being imaged corresponds to an example where an image according to the biopsy needle is included. Furthermore, in this embodiment, the image 82A of the object of interest being imaged corresponds to an example where an image according to the object of interest is included.

FIG. 8 is a schematic view of an example of the tomographic image 72 where the image 80A of the breast, the image 82A of the object of interest, and the image 84A of the needle are shown. As described above, the tomographic image 72 is a radiation image reconstructed based on a plurality of sheets of projection images 70, and thus includes a great amount of information (amount of electric charge) compared to one sheet of projection image 70. Since the amount of information is great, in the tomographic image 72, the image 82A of the object of interest is easily viewed compared to one sheet of projection image 70. On the other hand, since the needle is inserted in a direction intersecting the tomographic image 72, in the image 84A of the needle, a portion of the image 84A of the needle corresponding to a tomographic plane (the height of the tomographic image 72) is brought into focus. For this reason, the needle image 84A is displayed clearly, specifically, as a white image. However, an image of the needle corresponding to a portion different from the tomographic plane (the height of the tomographic image 72) may be generated as an artifact 89, and visibility of the entire image of the needle may be degraded. In this way, in the tomographic image 72, even if the image 82A of the object of interest can be visually recognized clearly, visibility of the image 84A of the needle is degraded, and it may be difficult to confirm the positional relationship between both of them, and in particular, the position of an opening of the needle for collecting an object of interest. Accordingly, in the radiation imaging system 10 (console 16) of this embodiment, a radiation image for facilitating the confirmation of the positional relationship between the object of interest and the needle is generated.

Next, in Step S204, the control unit 30 of the console 16 specifies the image 82A of the object of interest from the tomographic image 72. A method of specifying the image 82A of the object of interest is not particularly limited. For example, image analysis may be performed to specify the image 82A of the object of interest from the tomographic image 72. For example, the user may designate the image 82A of the object of interest in the tomographic image 72 displayed on the display unit 36 using the operating unit 40, and the control unit 30 may specify the image 82A of the object of interest based on the received designation (the designated position or the like). In this case, the I/F unit 44 functions as an example of a reception unit.

In this embodiment, although the image 82A of the object of interest is specified from the tomographic image 72, the image of the object of interest may be specified from the projection image 70. In this case, as a specification method, similarly to the tomographic image 72, the image of the object of interest may be specified from the projection image 70. When the image of the object of interest is specified from the projection image 70, it is preferable to use the projection image 70 captured by exposing radiation from the normal direction, that is, at the projection angle of 0°.

As a specification method, the tomographic image 72 may be synthesized (reconstructed) to generate a pseudo two-dimensional image corresponding to the projection image 70, and similarly to the tomographic image 72, the image of the object of interest may be specified from the generated pseudo two-dimensional image. In this case, similarly to a case where the image of the object of interest is specified from the projection image 70, it is preferable to use a two-dimensional image corresponding to the projection image 70 captured by exposing radiation from the normal direction, that is, at the projection angle of 0°. A method of generating a pseudo two-dimensional image is not limited, and for example, the same technique as the generation of a sectional image 74 described below in detail may be used.

Next, in Step S206, the control unit 30 of the console 16 generates a sectional image 74 including an image 82B of the object of interest and an image 84B of the needle. In this embodiment, the "section" refers to a surface in a direction intersecting the imaging surface 27. As a specific example of the surface in the direction intersecting the imaging surface 27, a surface perpendicular to the imaging surface 27 is given. In this step, since the radiation source 24 moves along the x-axis direction, the control unit 30 generates a sectional image 74 in a y-z-axis direction taking into consideration the influence of an artifact with the movement of the radiation source 24. Another sectional image 74, for example, a sectional image 74 in an x-z-axis direction or a sectional image 74 in an oblique direction may be generated according to the position (the image 82B of the object of interest) of the object of interest or the insertion direction or the position (the image 84B of the needle) of the needle.

The image 82B of the object of interest in the sectional image 74 generated by the control unit 30 is not the same image as the image 82A of the object of interest specified in Step S204 since the viewing direction (surface) is different even if the object of interest is the same. For this reason, the control unit 30 first determines the object of interest from the specified image 82B of the object of interest and detects an image including the determined object of interest by image analysis or the like.

A method of generating the sectional image 74 is not particularly limited. The sectional image 74 is a radiation image of the pseudo two-dimensional image reconstructed from the tomographic image. As a method of reconstructing and generating the sectional image 74 (pseudo two-dimensional image) from the tomographic image 72, for example, a technique described in US2010-0135558A may be used.

Similarly to the tomographic image 72, since the sectional image 74 includes information of a plurality of projection images 70, the image 82B of the object of interest may be easily viewed, while visibility of the image 84B of the needle may be degraded.

Next, in Step S208, the control unit 30 of the console 16 reprojects the projection image 70 to generate an image 84C of the needle. It is preferable that the projection image 70 for generating the image 84C of the needle is an image where the image of the needle is visually viewed most easily. In this embodiment, as described above, since the radiation source 24 moves along the x-axis direction, the projection image 70 captured at a projection angle which is the greatest projection angle and corresponds to the side separated from the needle is preferably used. In the case of imaging schematically shown in FIG. 5, the needle is positioned at the imaging position P1 side and inserted obliquely from the P1 side to the PN side. Accordingly, it is preferable to generate the image 84C of the needle from the projection image 70 captured at the greatest projection angle (imaging position) PN corresponding to the side separated from the needle rather than the projection image 70 captured from the greatest projection angle (imaging position) P1 corresponding to the side close to the needle. For this reason, the projection image 70 captured from PN in advance is determined as the projection image 70 for generating the image 84C of the needle in advance.

In this embodiment, since the radiation source 24 moves along the x-axis direction, in imaging schematically shown in FIG. 5, the projection image 70 captured from the imaging position (projection angle) PN is preferably used; however, if the moving direction of the radiation source 24 is different, the projection angle of the projection image 70 is different. As described above, it is preferable that the projection image 70 for generating the image 84C of the needle is determined taking into consideration the moving direction of the radiation source 24.

For the reason described above, in many cases, the image of the needle in the projection image 70 has high visibility compared to the needle images 84A and 84B in the tomographic image 72 and the sectional image 74. For this reason, in many cases, the image 84C of the needle generated from the projection image 70 has high visibility compared to the needle images 84A and 84B in the tomographic image 72 and the sectional image 74.

Next, in Step S210, the control unit 30 of the console 16 synthesizes the generated image 84C of the needle into the sectional image 74 generated in Step S206. A synthesis method is not particularly limited. In this embodiment, the control unit 30 synthesizes the generated image 84C of the needle to be overlaid on the sectional image 74. When synthesizing the image 84C of the needle, it is preferable that the position of the image 84C of the needle in the sectional image 74 is specified and the image 84C of the needle is synthesized at the specified position.

In the control unit 30 of this embodiment, when synthesizing the image 84C of the needle, enhancement processing for enhancing the image 84C of the needle is performed. The enhancement processing is not particularly limited, and for example, processing for changing the color of the image 84C of the needle to a conspicuous color or for enhancing the color near the opening for collecting the object of interest is given.

In this way, the image 84C of the needle with high visibility generated from the projection image 70 is synthesized into the sectional image 74 including the image 82B of the object of interest with high visibility, whereby the positional relationship between the object of interest and the needle is easily confirmed.

Next, in Step S212, the control unit 30 of the console 16 displays the sectional image 74 with the image 84C of the needle synthesized thereinto on the display unit 36 and then ends the position confirmation processing of Step S112.

If the position confirmation processing of Step S112 ends, the process progresses to Step S114. In Step S114, it is determined whether or not to retry the insertion of the needle. The user confirms the positional relationship between the object of interest and the needle by the sectional image displayed on the display unit 36 with the image 84 of the needle synthesized thereinto by the processing of Step S212 described above, and when it is determined that the positional relationship is inappropriate, that is, there is a possibility that an object of interest cannot be appropriately collected, the user retries to insert the needle into the breast. In this embodiment, when retrying the insertion of the needle, the user instructs the effect by the operating unit 40. When an instruction to retry is received, the control unit 30 returns to Step S108 and repeats this processing. When retrying is not performed, the process progresses to Step S116.

In Step S116, after a tissue of the object of interest is sucked and resected by the needle, this processing ends.

Second Embodiment

In the first embodiment, a case where the control unit 30 reprojects the projection image 70 determined in advance to synthesize the image 84C of the needle has been described. In this embodiment, a case where the image 84C of the needle is generated from the projection image 70 designated by the user will be described.

In the first embodiment, although the image of the needle is generated from the projection image 70 captured at a predetermined projection angle at which the image of the needle is assumed to be visually recognized easily, in the projection image 70 at a projection angle other than the predetermined projection angle, the image of the needle may be visually recognized easily, or the positional relationship of the object of interest may be understood easily. In the radiation imaging system 10 of this embodiment, a case where the image (the projection image 70 from which the image of the needle is extracted) of the needle is selectable by the user in this case will be described.

The configurations of the radiation imaging system 10, the radiation imaging device 12, the console 16, and the radiation image reading device 20 are the same as those in the first embodiment. The same configurations and operations as those in the first embodiment are represented by the same reference numerals, and detailed description thereof will not be repeated.

In the radiation imaging system 10 of this embodiment, position confirmation processing which is executed by the control unit 30 of the console 16 in a biopsy is different from that in the first embodiment (see FIG. 4). For this reason, the position confirmation processing of this embodiment will be described in detail.

FIG. 9 is a flowchart showing an example of position confirmation processing which is executed by a control unit of a console of the second embodiment. As shown in FIG. 9, the position confirmation processing of this embodiment has Steps S207A and S207B between Step S206 and Step S208 of the position confirmation processing of the first embodiment.

In Steps S200 to S206, as in the first embodiment, if the control unit 30 of the console 16 acquired N sheets of projection images 70, the tomographic image 72 is reconstructed based on a plurality of acquired projection images 70 to generate the tomographic image 72 parallel to the imaging surface 27 at a predetermined slice thickness and is displayed on the display unit 36. The control unit 30 of the console 16 specifies the image 82A of the object of interest from the tomographic image 72 or the projection image 70 and generates the sectional image 74 including the image 82B of the object of interest and the image 84B of the needle.

In the position confirmation processing of this embodiment, after Step S206, the process progresses to Step S207A. In Step S207A, the control unit 30 of the console 16 displays the projection image 70 on the display unit 36. A way of displaying is not particularly limited. For example, all or a part of a plurality of acquired projection images 70 may be displayed in parallel on the display unit 36, or one projection image 70 may be displayed on the display unit 36 and the projection image 70 at a different projection angle may be sequentially switched according to a user's instruction.

The user confirms the projection image 70 displayed on the display unit 36 and selects at least one projection image 70, in which the image of the needle is easily confirmed, by the operating unit 40. Alternatively, the projection image 70 or the like in which the positional relationship between the image of the needle and the image of the object of interest is easily understood is selected by the operating unit 40. The selected projection image 70 may be one, or two or more.

Next, in Step S207B, it is determined whether or not the projection image 70 is selected by the user, and when the projection image 70 is selected, the process progresses to Step S208.

In Steps S208 to S212, as in the first embodiment, the control unit 30 of the console 16 reprojects the projection image 70 to generate the image 84C of the needle, synthesizes the generated image 84C of the needle into the sectional image 74 generated in Step S206, displays the sectional image 74 with the image 84C of the needle synthesized thereinto on the display unit 36, and then, ends the position confirmation processing of this embodiment.

In this way, in the radiation imaging system 10 of this embodiment, the projection image 70 is selected from a plurality of projection images 70, thereby selecting the image 84 of the needle for use in confirming the positional relationship between the object of interest and the needle; therefore, it is possible to easily confirm the positional relationship between the object of interest and the needle according to the user's desire. In the radiation imaging system 10 of this embodiment, the user can select the projection image 70 (the image of the needle) while confirming the tomographic image 72 having the object of interest with high visibility displayed on the display unit 36; therefore, the projection image 70 (the image of the needle) is easily selected.

As described above, in the respective embodiments described above, in the radiation imaging system 10 using the radiation imaging device 12 as a mammography device, when performing a biopsy of the breast of the subject, the positional relationship between the object of interest and the needle is confirmed using a radiation image obtained through tomosynthesis imaging. The control unit 30 of the console 16 reconstructs the projection image 70 obtained through tomosynthesis imaging to generate the tomographic image 72 parallel (an x-y-axis direction) to the imaging surface 27 in a state where the needle is inserted into the breast, and specifies the image 82A of the object of interest from the tomographic image 72. The control unit 30 of the console 16 generates the sectional image 74 which includes the specified image 82B of the object of interest and the image 84B of the needle and intersects the imaging surface 27. In the respective embodiments described above, as a specific example, the sectional image 74 in a y-x-axis direction is generated. In addition, the control unit 30 of the console 16 generates the image 84C of the needle from the projection image 70, synthesizes the generated image 84C of the needle into the sectional image 74 while aligning, and displays the sectional image 74 on the display unit 36.

In the tomographic image or the sectional image, since the amount of information is great, the image of the object of interest is an image with high visibility. When performing tomosynthesis imaging, in particular, unlike CT, if the radiation imaging device is a mammography device, an imaging angle range is narrow; therefore, visibility of the image of the needle included in the tomographic image or the sectional image may be degraded due to the needle being inserted in a direction intersecting the tomographic image. In particular, there is concern that visibility near the tip (the opening for collecting the object of interest) of the needle is degraded.

In a stereo image, the image of the needle has high visibility compared to the tomographic image or the sectional image; however, since the amount of information becomes small, the image of the object of interest may be degraded.

When performing two times of imaging including imaging of the projection image for obtaining the tomographic image or the sectional image having the image of the object of interest with high visibility and imaging of a stereo image having the image of the needle with high visibility, a burden imposed on the subject is increased.

In contrast, in the radiation imaging system 10 of the respective embodiments described above, a sectional image having the image of the object of interest with high visibility and the image of the needle generated from the projection image corresponding to the stereo image having the image of the needle with high visibility are synthesized through single tomosynthesis imaging. With this, in the radiation imaging system 10 of this embodiment, a sectional image in which both of the image of the object of interest and the image of the needle (in particular, the opening) have high visibility can be obtained; therefore, the positional relationship between the object of interest and the needle is easily confirmed.

A sectional image in which both of the image of the object of interest and the image of the needle (in particular, the opening) have high visibility can be obtained through single tomosynthesis imaging; therefore, it is possible to suppress a burden imposed on the subject.

In the respective embodiments described above, although the image 84C of the needle generated from the projection image 70 is synthesized on the sectional image 74, a synthesis method is not particularly limited as described above. For example, the image 84B of the needle in the sectional image 74 may be deleted or the like, and the image 84C of the needle generated from the projection image 70 may be replaced and synthesized.

In the respective embodiments described above, although the image 84C of the needle generated from the projection image 70 is synthesized into the sectional image 74, for example, the control unit 30 of the console 16 may synthesize a created image (illustration) of the needle or an image (an image by a photograph) of the needle stored in the console 16 in advance. When performing synthesis in this way, if the control unit 30 can recognize the state (position and angle, and the like) of the needle by the imaging menu, the biopsy unit (not shown), or the like, an image according to the state of the needle is preferably used.

In the respective embodiments described above, although a case where the control unit 30 of the console 16 has a function as a tomographic image generation unit which generates the tomographic image 72 from the projection image 70, a function as a specification unit which specifies the image 82A of the object of interest from the tomographic image 72, a function as a sectional image generation unit which generates the sectional image 74, and a function as a synthesis unit which generates the image 84C of the needle from the projection image 70 and synthesizes the image 84C of the needle into the sectional image 74 has been described, the invention is not limited thereto. For example, the control unit 50 of the radiation image reading device 20 may have the respective functional units. A part of the functional units may be provided in the control unit 30 of the console 16, and the other functional units may be provided in the control unit 50 of the radiation image reading device 20.

In the radiation imaging system 10 of the respective embodiments described above, although a case where the radiation imaging device 12 is a mammography device has been described, other radiation imaging devices may be provided. The object is not limited to the breast of the subject, and other regions may be provided, and are not particularly limited.

Radiation which is used to capture the radiation image is not particularly limited, and X-rays, γ-rays, or the like can be applied.

In addition, the configurations and the operations of the radiation imaging system 10, the radiation imaging device 12, the console 16, and the radiation image reading device 20 described in the respective embodiments described above are an example, and may be changed according to the situation without departing from the gist of the invention. The flow of the biopsy or the flow of the position confirmation processing described in the respective embodiments described above is an example, and may be changed according to the situation without departing from the gist of the invention.

With respect to the respective embodiments described above, the following supplementary note is disclosed.

(Supplementary Note 1)

An image processing method includes acquiring a plurality of projection images from a radiation imaging device which includes a radiation detector configured to detect radiation and an imaging stand configured to include the radiation detector, and exposes a breast in a state where the breast placed on an imaging surface of the imaging stand and a biopsy needle inserted into the breast to radiation at each of different projection angles to capture the plurality of projection images by the radiation detector, causing a tomographic image generation unit to generate a plurality of tomographic images based on the plurality of captured projection images, causing a specification unit to specify an image of an object of interest from one of the projection image captured from a direction normal to the imaging surface, the tomographic image generated by the tomographic image generation unit, and a pseudo two-dimensional image reconstructed based on the tomographic image, causing a sectional image generation unit to generate a sectional image of a section intersecting the imaging surface and including an image according to the object of interest specified by the specification unit, and causing a synthesis unit to generate an image of the biopsy needle and synthesizes the generated image of the biopsy needle on the sectional image generated by the sectional image generation unit.

What is claimed is:

1. A radiation imaging system comprising:
   a radiation imaging device which includes a radiation detector configured to detect radiation and an imaging stand configured to include the radiation detector, and exposes a breast in a state where the breast placed on an imaging surface of the imaging stand and a biopsy needle is inserted into the breast to radiate at each of different projection angles to capture a plurality of projection images by the radiation detector; and a processor configured to:

generate a plurality of tomographic images in a single imaging pass, based on the plurality of captured projection images;

specify an image of an object of interest from one of the projection image captured from a direction normal to the imaging surface, the tomographic image which was generated, and a pseudo two-dimensional image reconstructed based on the tomographic image;

generate a sectional image of a section intersecting the imaging surface and including an image according to the object of interest which is specified; and generate an image of the biopsy needle from the single imaging pass and synthesize the generated image of the biopsy needle on the sectional image which is generated.

2. The radiation imaging system according to claim 1, wherein the processor is further configured to:

generate a sectional image including an image according to the object of interest which is specified and an image according to the inserted biopsy needle, and generate an image of the biopsy needle and synthesize the image of the biopsy needle on the image of the biopsy needle in the sectional image.

3. The radiation imaging system according to claim 1, wherein the processor is further configured to reproject the plurality of tomographic images which are generated onto a section in a direction intersecting the imaging surface to generate the sectional image.

4. The radiation imaging system according to claim 2, wherein the processor is further configured to reproject the plurality of tomographic images which are generated onto a section in a direction intersecting the imaging surface to generate the sectional image.

5. The radiation imaging system according to claim 1, wherein the processor is further configured to extract and generate the image of the biopsy needle from one of the plurality of projection images and synthesize the image of the biopsy needle into the sectional image.

6. The radiation imaging system according to claim 2, wherein the processor is further configured to extract and generate the image of the biopsy needle from one of the plurality of projection images and synthesize the image of the biopsy needle into the sectional image.

7. The radiation imaging system according to claim 3, wherein the processor is further configured to extract and generate the image of the biopsy needle from one of the plurality of projection images and synthesize the image of the biopsy needle into the sectional image.

8. The radiation imaging system according to claim 4, wherein the processor is further configured to extract and generate the image of the biopsy needle from one of the plurality of projection images and synthesize the image of the biopsy needle into the sectional image.

9. The radiation imaging system according to claim 5, wherein the processor is further configured to extract the image of the biopsy needle from a projection image corresponding to a projection angle which is the greatest projection angle among the different projection angles and corresponds to a side separated from the biopsy needle.

10. The radiation imaging system according to claim 6, wherein the processor is further configured to extract the image of the biopsy needle from a projection image corresponding to a projection angle which is the greatest projection angle among the different projection angles and corresponds to a side separated from the biopsy needle.

11. The radiation imaging system according to claim 7, wherein the processor is further configured to extract the image of the biopsy needle from a projection image corresponding to a projection angle which is the greatest projection angle among the different projection angles and corresponds to a side separated from the biopsy needle.

12. The radiation imaging system according to claim 8, wherein the processor is further configured to extract the image of the biopsy needle from a projection image corresponding to a projection angle which is the greatest projection angle among the different projection angles and corresponds to a side separated from the biopsy needle.

13. The radiation imaging system according to claim 1, wherein the section is a surface in a direction perpendicular to the imaging surface.

14. The radiation imaging system according to claim 1, further comprising:

a reception unit which receives the designation of an image of an object of interest from one of the projection image, the tomographic image, and the pseudo two-dimensional image, wherein the processor is further configured to specify the image of the object of interest based on the designation of the image of the object of interest received by the reception unit.

15. The radiation imaging system according to claim 1, wherein the processor is further configured to perform enhancement processing for enhancing the image of the biopsy needle to be synthesized.

16. The radiation imaging system according to claim 1, further comprising:

a display unit which displays the sectional image with the image of the biopsy needle which is synthesized.

17. The radiation imaging system according to claim 1, wherein the processor is further configured to:

display the plurality of projection images on the display unit, receive the designation of a projection image used to generate the image of the biopsy needle from the plurality of displayed projection images, and generate the image of the biopsy needle from the projection image which is received.

18. A radiation imaging system comprising:

a radiation imaging device which includes a radiation detector configured to detect radiation and an imaging stand configured to include the radiation detector, and exposes a breast in a state where the breast placed on an imaging surface of the imaging stand and a biopsy needle inserted into the breast to radiation at respective different projection angles to capture a plurality of projection images at the respective projection angles by the radiation detector; and a processor configured to:

specify an image of an object of interest from the projection image captured in a direction normal to the imaging surface;

generate a sectional image of a section intersecting the imaging surface and including an image according to the object of interest which is specified; and generate an image of the biopsy needle from a single imaging pass, synthesize the generated image of the biopsy needle on the sectional image which is generated, and display the synthesized sectional image on a display unit.

19. An image processing device which is used in the radiation imaging system according to claim 1, the image processing device comprising:

the processor configured to:

generate the plurality of tomographic images reconstructed based on projection images obtained by imaging the breast at different projection angles in a state where the biopsy needle collecting the object of interest is inserted into the breast;

specify the image of the object of interest from one of the projection image, the tomographic image, and the pseudo two-dimensional image reconstructed based on the tomographic image;

generate the sectional image of the section intersecting the tomographic image and including the image according to the object of interest which is specified; and generate the image of the biopsy needle, synthesize the generated image of the biopsy needle on the sectional image, and display the synthesized sectional image on a display.

20. A non-transitory computer-readable recording medium having an image processing program recorded thereon, the image processing program causing a computer to execute processing for, using the radiation imaging system according to claim 1:

acquiring the plurality of projection images from the radiation imaging device which includes the radiation detector configured to detect radiation and the imaging stand configured to include the radiation detector, and exposes the breast in the state where the breast placed on an imaging surface of the imaging stand and the biopsy needle inserted into the breast to radiation at each of different projection angles to capture the plurality of projection images by the radiation detector;

generating the plurality of tomographic images based on the plurality of captured projection images;

specifying the image of the object of interest from one of the projection image captured in the direction normal to the imaging surface, the tomographic image, and the pseudo two-dimensional image reconstructed based on the tomographic image;

generating the sectional image of the section intersecting the imaging surface and including the specified image according to the object of interest; and generating the image of the biopsy needle and synthesizing the generated image of the biopsy needle on the sectional image.

* * * * *